United States Patent [19]
Hodgson et al.

[11] Patent Number: 5,345,945
[45] Date of Patent: Sep. 13, 1994

[54] DUAL COIL GUIDEWIRE WITH RADIOPAQUE DISTAL TIP

[75] Inventors: William S. Hodgson, Cohasset, Mass.; Jagdish C. Dhuwalia, Irvine; Russell Pflueger, Laguna Niguel, both of Calif.

[73] Assignee: Baxter International Inc., Deerfield, Ill.

[21] Appl. No.: 143,546

[22] Filed: Dec. 25, 1993

Related U.S. Application Data

[63] Continuation of Ser. No. 865,417, Apr. 8, 1992, abandoned, which is a continuation-in-part of Ser. No. 644,802, Jan. 22, 1991, abandoned, which is a continuation-in-part of Ser. No. 574,629, Aug. 29, 1990, abandoned.

[51] Int. Cl.$^5$ ............................................... A61B 5/00
[52] U.S. Cl. .................................. 128/772; 604/280; 604/282; 128/656
[58] Field of Search ............... 128/657, 772; 604/164, 604/170, 280, 282

[56] References Cited

U.S. PATENT DOCUMENTS

| | | |
|---|---|---|
| 3,528,406 | 9/1970 | Jeckel et al. . |
| 3,749,086 | 7/1973 | Kline et al. . |
| 3,789,841 | 2/1974 | Antoshkiw . |
| 4,020,829 | 5/1977 | Wilson et al. . |
| 4,345,602 | 8/1982 | Yoshimura et al. . |
| 4,471,779 | 8/1984 | Antoshkiw et al. . |
| 4,490,421 | 12/1984 | Levy . |
| 4,534,363 | 8/1985 | Gold . |
| 4,538,622 | 9/1985 | Samson et al. . |
| 4,545,390 | 10/1985 | Leary . |
| 4,548,206 | 10/1985 | Osborne . |
| 4,554,929 | 11/1985 | Samson et al. . |
| 4,573,470 | 3/1986 | Samson et al. . |
| 4,586,923 | 5/1986 | Gould et al. . |
| 4,601,705 | 7/1986 | McCoy . |
| 4,616,653 | 10/1986 | Samson et al. . |
| 4,619,263 | 10/1986 | Frisbie et al. . |
| 4,641,654 | 2/1987 | Samson et al. . |
| 4,646,719 | 3/1987 | Neuman et al. . |
| 4,646,742 | 3/1987 | Packard et al. . |
| 4,715,378 | 12/1987 | Pope, Jr.; et al. . |
| 4,719,924 | 1/1988 | Crittenden et al. ............... 128/657 |
| 4,721,117 | 1/1988 | Mar et al. . |
| 4,723,936 | 2/1988 | Buchbinder et al. . |
| 4,763,647 | 8/1988 | Gambale . |

(List continued on next page.)

FOREIGN PATENT DOCUMENTS

| | | |
|---|---|---|
| 1208096 | 7/1986 | Canada . |
| 0213748 | 3/1987 | European Pat. Off. . |
| 0213751 | 8/1987 | European Pat. Off. . |
| 0259945 | 3/1988 | European Pat. Off. . |
| 0145489 | 6/1989 | European Pat. Off. . |
| 3833365 | 9/1988 | Fed. Rep. of Germany . |
| 3931350 | 9/1989 | Fed. Rep. of Germany . |
| 86/06285 | 11/1986 | PCT Int'l Appl. . |
| WO90/05486 | 5/1990 | PCT Int'l Appl. . |
| 2028136 | 3/1980 | United Kingdom . |
| 2098073 | 11/1982 | United Kingdom . |
| 2127294 | 11/1986 | United Kingdom . |
| 2180454 | 4/1987 | United Kingdom . |
| WO90/07355 | 7/1990 | World Int. Prop. O. . |
| WO92/00775 | 1/1992 | World Int. Prop. O. . |
| WO92/04072 | 3/1992 | World Int. Prop. O. . |
| WO92/13483 | 8/1992 | World Int. Prop. O. . |

Primary Examiner—Lee S. Cohen
Assistant Examiner—Brian L. Casler
Attorney, Agent, or Firm—Raymond Sun; Debra Condino

[57] ABSTRACT

A guidewire having a centrally located core wire about which is mounted a single outer helical coil spring. The core wire is typically longer than the outer helical coil spring, with the helical coil spring and core wire having common distal ends. The spring is brazed at both its distal and proximal end to the core wire. The distal brazing of the core wire and helical coil springs is rounded. A second small radiopaque helical coil spring is fitted in the distal end of the outer helical coil spring and may be brazed to the core wire and outer helical coil spring.

17 Claims, 4 Drawing Sheets

U.S. PATENT DOCUMENTS

| | | |
|---|---|---|
| 4,808,164 | 2/1989 | Hess . |
| 4,813,434 | 3/1989 | Buchbinder et al. . |
| 4,815,478 | 3/1989 | Buchbinder et al. . |
| 4,827,941 | 5/1989 | Taylor et al. . |
| 4,846,186 | 7/1989 | Box et al. . |
| 4,886,067 | 12/1989 | Palermo . |
| 4,922,924 | 5/1990 | Gambale et al. . |
| 5,007,434 | 4/1991 | Doyle et al. . |
| 5,052,404 | 10/1991 | Hodgson ............... 128/272 |
| 5,060,660 | 10/1991 | Gamble et al. ............ 604/170 |
| 5,063,935 | 11/1991 | Gambale . |
| 5,065,769 | 11/1991 | De Toledo ............ 128/657 |
| 5,144,959 | 9/1992 | Gambale et al. . |
| 5,154,705 | 10/1992 | Fleischhacker et al. ........... 604/282 |
| 5,176,149 | 1/1993 | Grenouillet . |
| 5,178,158 | 1/1993 | de Toledo . |

DUAL COIL GUIDEWIRE WITH RADIOPAQUE DISTAL TIP

This application is a continuation of U.S. application Ser. No. 07/865,417 filed on Apr. 8, 1992, now abandoned, which is a continuation-in-part application of Ser. No. 07/644,802, filed Jan. 22, 1991, now abandoned, which is a continuation-in-part application of Ser. No. 07/574,629, filed Aug. 29, 1990, now abandoned.

BACKGROUND OF THE INVENTION

The present invention is directed at the field of guidewires. Specifically, the present invention concerns a guidewire having a radiopaque tip.

Generally, guidewires include one or more coil springs fixed about a solid or tubular central core wire. Usually, the distal end of the guidewire is shapeable. This shapeability allows the surgeon to bend the distal end before insertion in the vascular system in conformance with the tortuous pathway of the desired vascular system segment through which the guidewire is being manipulated.

Guidewires are principally used for manipulating catheters through a patient's vessels, i.e. blood vessels. One specific application is the proper placement of a catheter in a patient's vascular system for a procedure known as percutaneous transluminal coronary angioplasty (PTCA).

A typical PTCA procedure involves percutaneously inserting a guiding catheter distal tip into the cardiovascular system of a patient and advanced therein until the distal tip thereof is in the coronary artery. A guidewire is introduced through the guiding catheter and advanced into the patient's coronary vasculature until the distal end of the guidewire crosses the lesion to be dilated. A dilatation catheter having an inflatable balloon on the distal portion thereof is advanced over the previously introduced guidewire, with the guidewire slidably disposed within an inner lumen of the dilatation catheter, until the dilatation balloon is properly positioned across the lesion. Once in position across the lesion, the balloon is inflated to a predetermined size with radiopaque liquid at a relatively high pressure to compress the atherosclerotic plaque of the lesion against the inside of the artery wall. The balloon is then deflated so that the dilatation catheter can be removed and blood flow resumed through the dilated artery.

Examples of guidewire designs are disclosed in U.S. Pat. Nos. 4,545,390, issued to Leary on Oct. 8, 1985; 4,538,622, issued to Samson on Sep. 3, 1985; 3,789,841, issued to Antoshkiw on Feb. 5, 1974; 4,815,478, and 4,813,434, both of which issued to Buchbinder et al on Mar. 28, 1989 and Mar. 21, 1989, respectively; 4,922,924, issued to Gamble et al on May 8, 1990; 4,763,647, issued to Gambale on Aug. 16, 1988; 4,846,186, issued to Box on Jul. 11, 1989; and 4,886,067, issued to Palermo on Dec. 12, 1989, with the disclosures of such references concerning the description of the guidewire being incorporated herein by reference.

Numerous workers have devised guidewires to increase the steerability through the coronary system. For example, the tips are made more flexible by terminating the distal end of the core wire short of the distal end of the helical coil spring. A second inner helical coil spring is brazed at one end to the distal end of the core wire and at its opposite end to the distal end of the outer helical coil spring, see Gambale U.S. Pat. No. 4,763,647 and Palermo U.S. Pat. No. 4,886,067.

Steering of the guidewire through the patient's coronary system is usually accomplished by viewing the guidewire via X-Ray. Visibility of the guidewire is achieved by forming at least a portion of the guidewire from a radiopaque material. This may be accomplished by many different ways. For example, a radiopaque spring is mounted to the end of the guidewire as disclosed in U.S. Pat, No. 4,538,622. Other examples include forming the entire guidewire from a radiopaque spring.

While existing guidewires provide adequate steerability and radiopaqueness, further improvements are desirable.

SUMMARY OF THE INVENTION

The present invention is directed at a guidewire having a centrally located core wire about which is mounted a single outer helical coil spring. The core wire is typically longer than the outer helical coil spring, with the helical coil spring and core wire having common distal ends. The spring is brazed at both its distal and proximal end to the core wire. The distal brazing of the core wire and helical coil springs is rounded. A second smaller radiopaque helical coil spring is fitted in the outer helical coil spring and may be brazed to the core wire and/or the outer helical coil spring at a location proximal to the helical coil spring or coil wire distal end. Thus, the inner radiopaque helical coil spring may be free floating about the distal end of the core wire or may be brazed at its proximal end to the core wire or at its distal end to the outer helical coil spring or at both ends.

DESCRIPTION OF THE DRAWINGS

The present invention may be better understood and the advantages will become apparent to those skilled in the art by reference to the accompanying drawings, wherein like reference numerals refer to like elements in the several figures, and wherein.

DESCRIPTION OF THE PREFERRED EMBODIMENTS

Figure 1A:
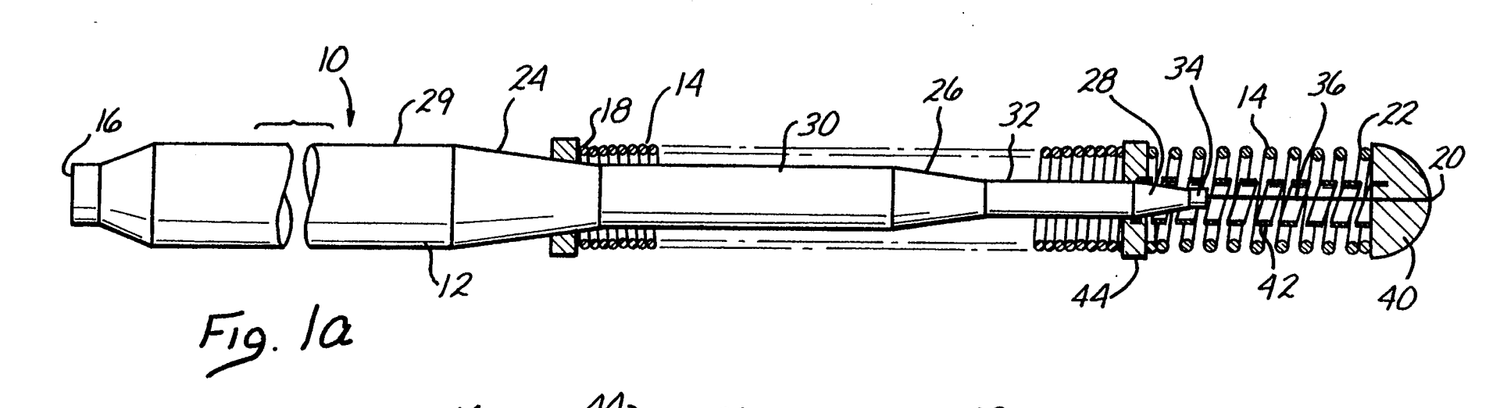
FIG. 1a is a cross-sectional side view of a guidewire in accordance with an embodiment of the invention.

The invention is directed at a guidewire as seen generally in FIG. 1a at 10. Guidewire 10 includes a centrally positioned core wire 12 and a outer helical coil spring 14. Centrally positioned core wire 12 and outer helical coil spring 14 have proximal ends 16 and 18, and distal ends 20 and 22, respectively. The distal ends 20 and 22 are generally commonly located, while the proximal end 18 is located distal of the proximal end 16.

Centrally positioned core wire 12 includes a main segment 29 from which extends multiple reduced diameter segments 30, 32 and 34. Proximally located and tapering to each of the reduced diameter segments 30, 32 and 34 are tapered portions 24, 26 and 28. At the very distal end of the centrally positioned core wire 12 is a tip portion 36. This tip portion 36 is of significantly smaller diameter in comparison to the distally located reduced diameter segment 34. This increases the flexibility of the tip portion 36. Preferably, tip portion 36 is flattened to provide for even greater flexibility. The outer diameters of the various segments of centrally positioned core wire 12, i.e. main segment 29 and reduced diameter segments 30, 32 and 34 is dependent upon the application of the finished guidewire 10. That is, the size of the vessel through which the guidewire 10 passes. This same rationale applies to the diameter or thickness for the tip portion 36.

The lengths of the main segment 29 and each reduced diameter segments 30, 32 and 34, is dependent upon the overall desired length for the guidewire 10. For example, main segment 29 may be 60", with reduced diameter segments 30, 32 and 34 having lengths of 7", 3" and 0.05". The tip portion 36 could be 0.7".

The outer helical coil spring 14 is brazed directly to centrally positioned core wire 12. Preferably the proximal end 18 of outer helical coil spring 14 is brazed at or near the first reduced diameter segment 30, such as at tapered portion 24 as seen at braze 38, with the distal end 22 brazed to the distal end 20 of centrally positioned core wire 12, as seen at 40. Brazed end 40 is rounded to reduce potential damage to a patient's vessels as the guidewire 10 is manipulated therethrough.

In accordance with the invention, a second radiopaque helical coil spring 42 is fitted in the outer helical coil spring 14. This second radiopaque helical coil spring 42 at its distal end is positioned at or near the distal end 22 and may be brazed directly to the centrally positioned core wire 12 and/or the outer helical coil spring 14 or left free floating about tip portion 36. As shown in FIG. 1a, one end of radiopaque helical coil spring 42 may be brazed directly to core wire 12 at proximal location 44, and the distal end may be brazed to outer helical coil spring 14 at a location proximal to distal end 20 at braze 40. The brazing at 44 provides an additional safety joint. That is, some guidewires have the distal end of the core wire terminating before the distal end of the outer helical coil spring.

Figure 1B:
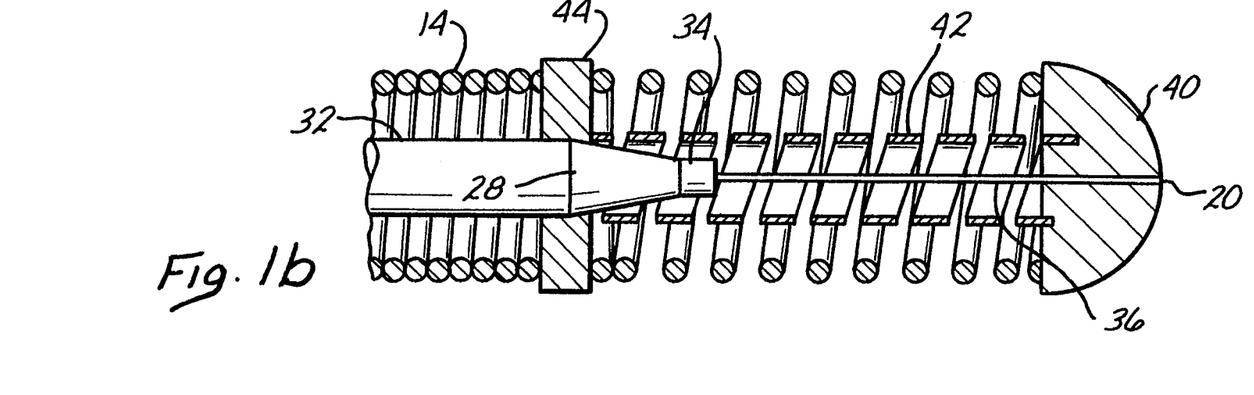
FIG. 1b is an enlarged sectional, cross section of the distal end of the guidewire of FIG. 1 illustrating an alternative mounting of the inner coil spring.

An alternative assembly of guidewire 10 is illustrated in FIG. 1b. In this embodiment inner radiopaque helical coil spring 42 is brazed at its distal end into brazed end 40 so that inner spring 42 is attached to both outer helical coil spring 14 and tip portion 36 of guidewire 10. The proximal end of inner radiopaque helical coil spring 42 is left unattached and is free to slide relative to tip portion 36 and the remaining portions of guidewire 10 including tapered portion 28 and reduced diameter segment 34. This provides an added degree of flexibility to the tip of guidewire 10 as opposed to the embodiment shown in FIG. 1a where both ends of inner radiopaque coil spring 42 are brazed into position. In either embodiment an added degree of safety in the event of tip breakage is achieved by insuring that at least a portion of the radiopaque coil 42 will remain with the tip portion, making a detached tip easier to locate under X-ray.

Figure 1C:
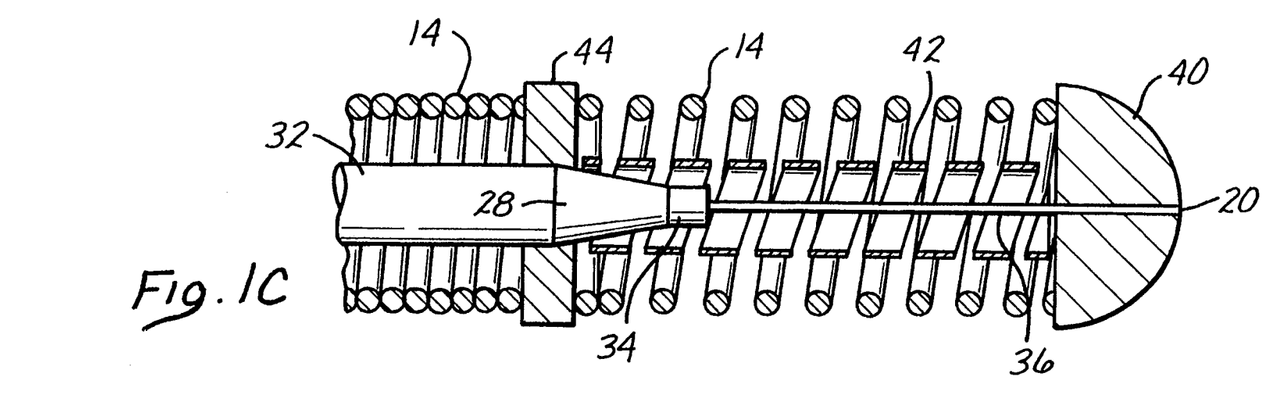
FIG. 1c is an enlarged sectional, cross section of the distal end of the guidewire of FIG. 1 illustrating an alternative mounting of the inner coil spring.
Figure 2:
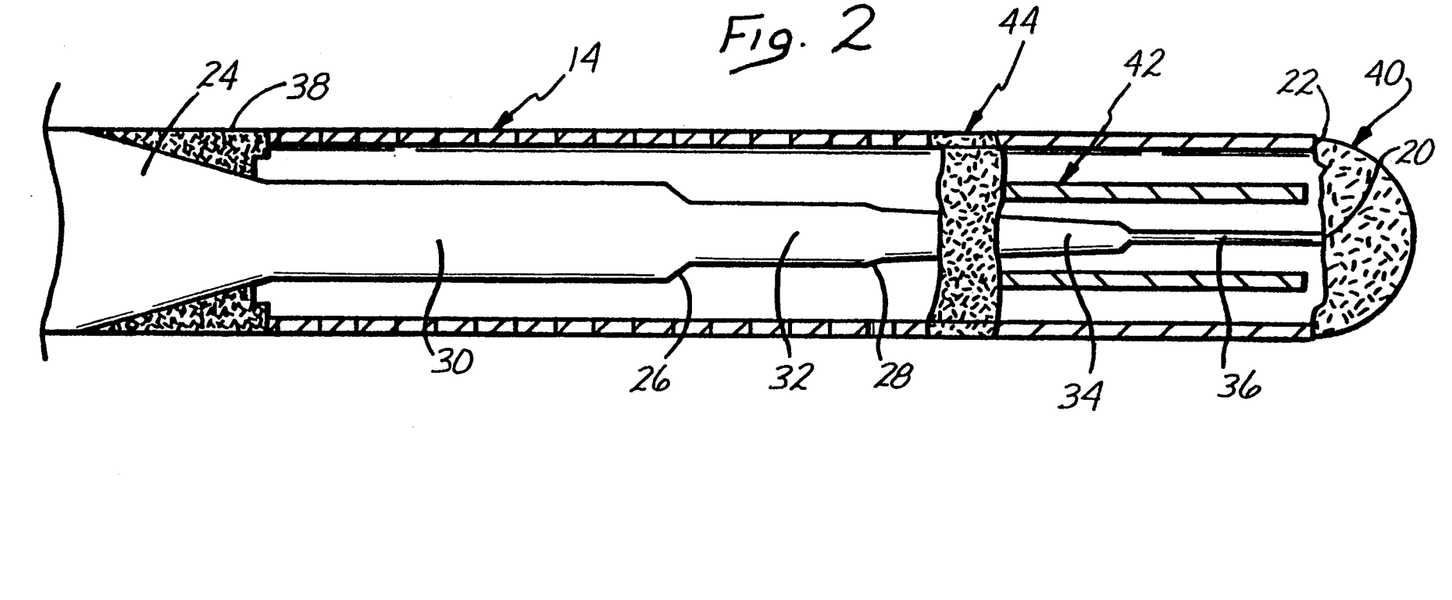
FIG. 2 is a sectional, cross section of the distal end of the guidewire of FIG. 1.

FIG. 1c illustrates an additional alternative construction of guidewire 10 wherein both ends of inner radiopaque helical coil spring 42 are left free so that coil spring 42 is free to slide relative to tip portion 36 within outer helical coil spring 14. This imparts the highest degree of tip flexibility while maintaining X-ray visualization.

Breakage of the outer helical coil spring could result in leaving this broken portion of the helical coil spring in the patient upon withdrawal of the guidewire. Attempts to correct this deficiency, as disclosed in Gambale '647 and Palermo '067 include the brazing of the opposite ends of an inner disposed helical coil spring to the distal ends of both the core wire and the outer helical coil spring. This has been suggested as improving the distal tip flexibility. However, breakage of the outer helical coil spring may still result in loss of a portion of the spring due to the lesser strength of the inner helical coil spring. The guidewire of the invention overcomes this deficiency by extending tip portion 36 through inner spring 42 and into brazed end 40. Thus, inner helical coil spring 42 does not have to function as a structural element holding the tip of guidewire 10 together. However, as noted above, either or both ends of radiopaque helical coil spring 42 may be brazed at brazing points 40 or 44 to provide added strength. It should be noted that brazing at brazed end 40 is preferred for ease of manufacturing and inspection purposes. Additionally, for purposes of enhanced flexibility it is preferred that only one end of radiopaque helical coil spring 42 be brazed.

The second radiopaque helical coil spring 42 is formed from a suitable material which does not appreciably reduce the overall flexibility of the guidewire 10 distal tip. For example, the second radiopaque helical coil spring 42 may be formed from Rhenium, Tungsten, Tantalum, Platinum or Gold. The outer helical coil spring 14 is typically formed from stainless steel.

The centrally positioned core wire 12 will have a increasing flexibility from the first reduced diameter segment 30 through the last segment 34. The outer helical coil spring 14 will have the same degree of flexibility along its entire length. The resulting flexibility of the guidewire 10 increases in a direction from the proximal end to the distal end due to the increase in flexibility of the centrally positioned core wire 12 from its proximal to distal ends. The distal tip of the guidewire 10 has a greater flexibility than the remainder of the guidewire 10 due to the flattening of the tip portion 36. Preferably the second radiopaque helical coil spring 42 is formed with adjacent coils spaced apart to provide for greater flexibility. It should be noted that the second radiopaque helical coil spring 42 is only providing the radiopaque feature. This spring 42 need not provide any degree of stiffness to the guidewire 10 distal end so that the coils may be sufficiently spaced apart from adjacent coils to provide the distal end with a high degree of flexibility.

Figure 3:
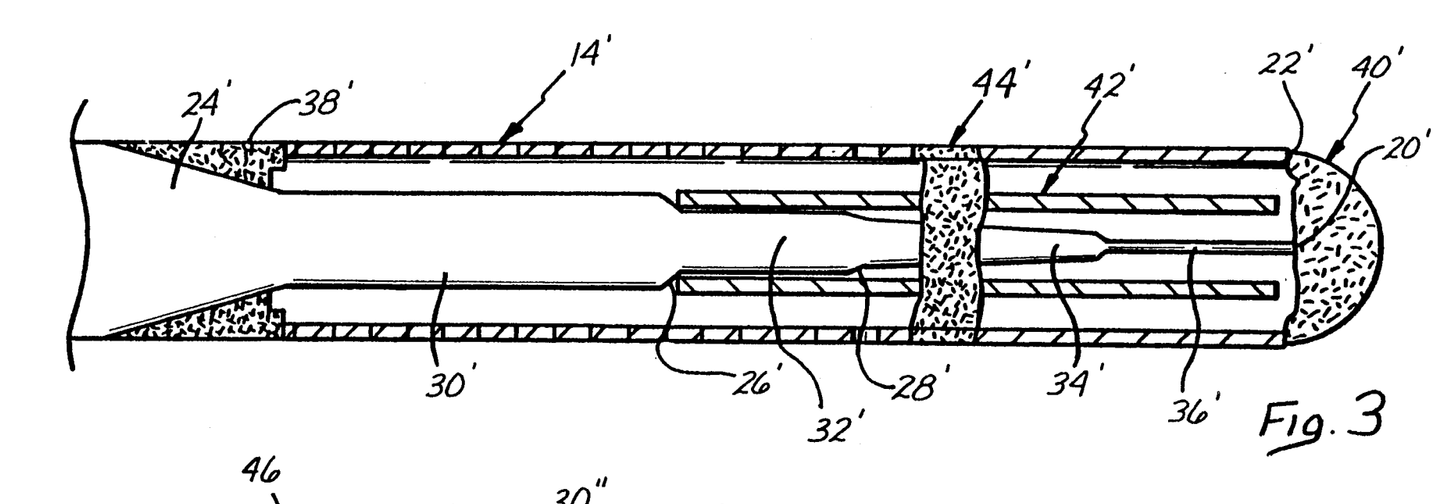
FIG. 3 is a sectional cross section of a distal end of a guidewire in accordance with another embodiment of the invention.

The overall length of the second radiopaque helical coil spring 42 is from about two to four centimeters. As seen in FIG. 3, the second radiopaque helical coil spring 42' may in fact extend proximal the brazing 44. The remaining elements of the guidewire 10' are essentially the same as the already described guidewire 10, with like reference numeral indicating like elements.

Figure 4:
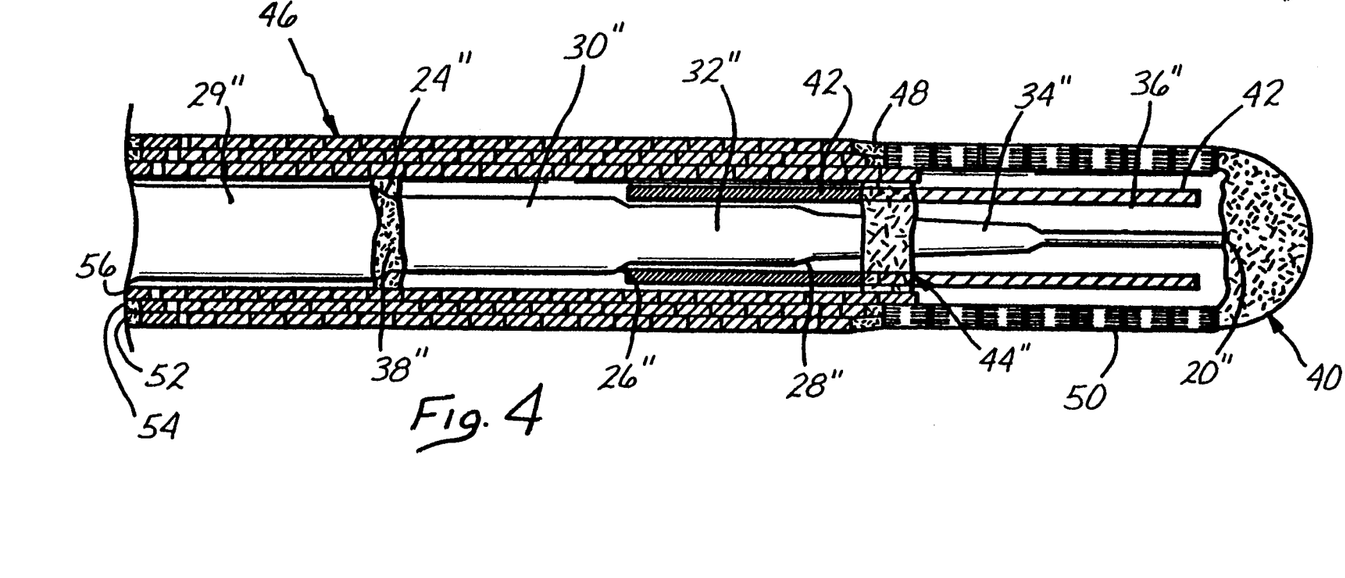
FIG. 4 is a further section cross section of a distal end of a guidewire in accordance with a still further embodiment of the invention.

While the described embodiments provide for a single outer helical coil spring 14, other embodiments are contemplated. This embodiment, seen in FIG. 4, replaces a portion of the outer helical coil spring 14 with a multiple helical coil spring arrangement, referred to as a trilayered spring 46. The trilayered spring 46 is formed by inserting one spring inside another, with this arrangement inserted into a third spring. This may be repeated to provide a multiple layered helical coil spring arrangement. One embodiment involves a three layered helical coil spring positioned one inside another as seen in FIG. 4 as spring layers 52, 54 and 56. This spring arrangement is purchased from MicroSpring Company of Norwell, Mass. under the product name Triplex. A more detailed description of such a trilayered spring 46 is found in U.S. Ser. No. 07/318,628, filed on Mar. 2, 1989 entitled TORQUE TRANSMITTER, which description is incorporated herein by reference.

The distal end of the trilayered spring 46, seen generally at 48 terminates proximal to the distal end 20" of the centrally positioned core wire 12. This distal end 48 is typically positioned adjacent the brazing 44". A separate helical coil spring 50 is brazed at one end to the trilayered spring 46 and at the opposite end to the distal end 20 of centrally positioned core wire 12. This helical coil spring 50 may be formed by extending one of the multiple springs to the distal end of the guidewire 10.

The remaining element of the guidewire 10' shown in FIG. 4 are the same as those shown in the previous embodiments, with like reference numeral referring to like elements.

Figure 5A:
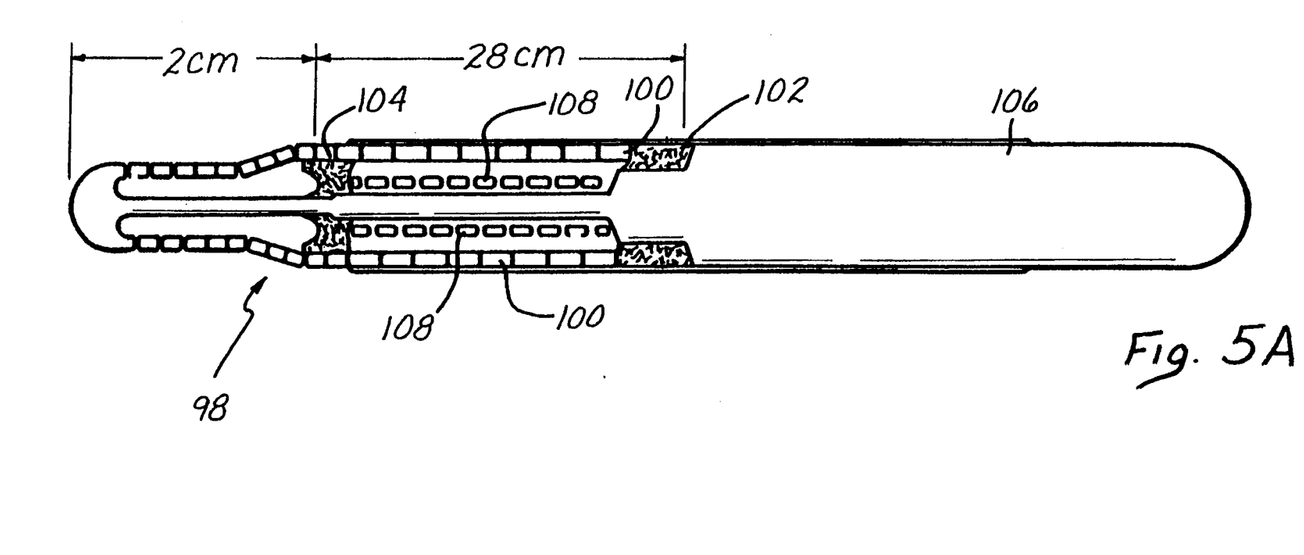
FIG. 5a is a further embodiment of the invention.

A still further embodiment of the invention is seen generally in FIG. 5a, at 98. In this embodiment an outer helical coil spring 100 is brazed at locations 102 and 104 to the inner core wire 106. Placed between these two brazing locations 102 and 104, and between the helical spring 100 and the core wire 106 is radiopaque coil 108. As with the previously discussed embodiments of guidewire 10, either or both ends of coil 108 may be, or may not be brazed directly to the core wire 106, preferably, coil 108 is freely moveable between the two brazed locations 102 and 104.

Figure 5B:
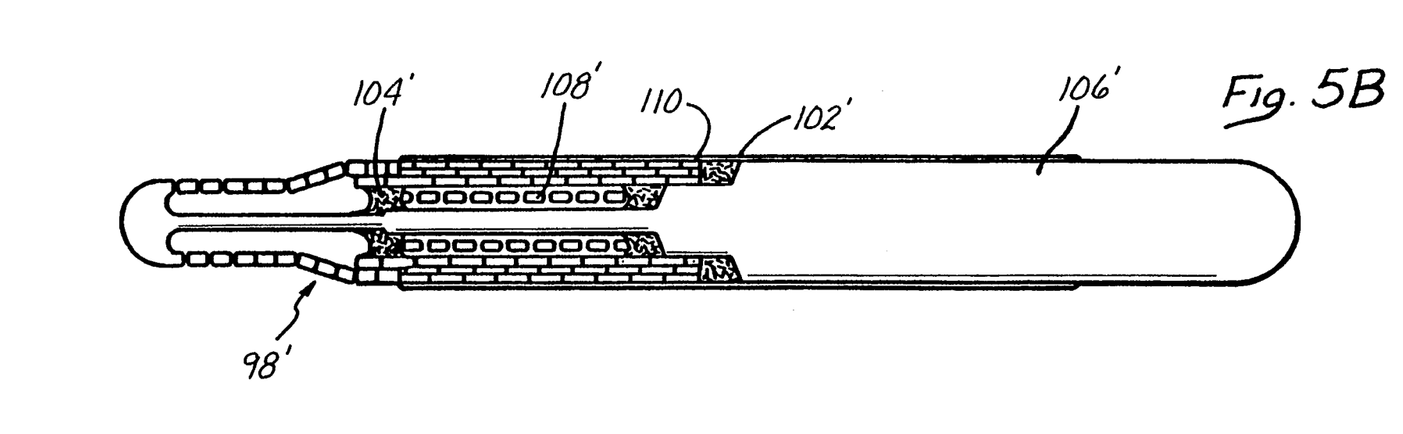
FIG. 5b is a still further embodiment of the invention.

FIG. 5b is a modification of the guidewire embodiment illustrated in FIG. 5a. The distinction is that the outer helical coil spring 100 is replaced with a trilayered spring assembly 110, similar to that described above for the embodiment of FIG. 4. The remaining elements of the guidewire 98' are indicated with prime numbers similar to those used in FIG. 5a.

While the preferred embodiments have been described, various modifications and substitutions may be made thereto without departing from the scope of the invention. Accordingly, it is to be understood that the invention has been described by way of illustration and not limitation.

What is claimed is:

1. A guidewire comprising:
a core wire having proximal and distal ends;
at least a first helical coil spring fit about said core wire, said helical coil spring having proximal and distal ends, with said helical coil spring proximal end secured to said core wire at a location distal said core wire proximal end, and said helical coil spring distal end secured to said core wire distal end; and
a second helical coil spring dimensioned to fit within said first helical coil spring and having a distal end and a free proximal end, said second helical coil spring at said distal end thereof being located at the distal end of said first helical coil spring, said second helical coil spring formed from a radiopaque material.

2. The guidewire of claim 1 wherein said second helical coil spring is from two to four centimeters in length.

3. The guidewire of claim 1 further including a rounded tip portion at said distal end of said helical coil spring and core wire.

4. The guidewire of claim 3 wherein said tip portion is secured to said distal ends of said core wire and first helical coil spring.

5. The guidewire of claim 4 wherein said second helical coil spring is formed from Rhenium, Tungsten, Tantalum, Platinum or Gold.

6. The guidewire of claim 1 wherein said second helical coil spring is formed from Rhenium, Tungsten, Tantalum, Platinum or Gold.

7. The guidewire of claim 1, further comprising:
a rounded tip portion at said distal end of said first helical coil spring and core wire,
wherein said second helical coil spring has proximal and distal ends, and
wherein said distal end of said second helical coil spring is secured to said tip portion.

8. A guidewire comprising:
a core wire having proximal and distal ends;
at least a first multilayered helical coil spring fit about said core wire, said helical coil spring having proximal and distal ends, with said helical coil spring proximal end secured to said core wire at a location distal said core wire proximal end, and said helical coil spring distal end terminating short of said core wire distal end;
a second helical coil spring fit about said core wire, said second helical coil spring having proximal and distal ends, with said second helical coil spring proximal end secured to said first multilayered helical coil spring distal end, and said second helical coil spring distal end secured to said core wire distal end; and
a third helical coil spring dimensioned to fit within said second helical coil spring, said third helical coil spring located at the distal end of said second helical coil spring and secured to said second helical coil spring and said core wire at a location proximal said distal ends of said core wire and second coil spring, said third helical coil spring formed from a radiopaque material.

9. The guidewire of claim 8 wherein said second helical coil spring is from two to four centimeters in length.

10. The guidewire of claim 8 wherein said second helical coil spring is formed from Rhenium, Tungsten, Tantalum, Platinum or Gold.

11. A guidewire comprising:
a core wire having proximal and distal ends;
a first helical coil spring fit about said core wire, said helical coil spring having proximal and distal ends, with said helical coil spring proximal end secured to said core wire at a location distal said core wire proximal end, and said helical coil spring distal end terminating short of said core wire distal end; and
a second helical coil spring of radiopaque material having a distal end and a free proximal end, said second coil spring being fit about said core wire between said first helical coil spring and said core wire with said distal ends of said first and said second coil springs generally radially aligned.

12. The guidewire of claim 11, further comprising:
a rounded tip portion at said distal end of said first helical coil spring and core wire,
wherein said second helical coil spring has proximal and distal ends, and
wherein said distal end of said second helical coil spring is secured to said tip portion.

13. A guidewire comprising:
a core wire having proximal and distal ends;
a first helical coil spring fit about said distal end of said core wire, said helical coil spring having proximal and distal ends, said helical coil spring proximal end secured to said core wire at a location distal to said core wire proximal end and said helical coil spring distal end being secured to said core wire at a position disposed adjacent to said core wire distal end;
a second helical coil spring having a distal end and a free proximal end, said second coil spring being fit about said core wire and disposed between said core wire and said first helical coil spring; and
said distal end of said second helical coil spring is secured at a position adjacent said distal end of said core wire.

14. The guidewire of claim 13 wherein said proximal end of said second coil spring is secured to said core wire.

15. The guidewire of claim 13 wherein both of said proximal and distal ends of said second helical coil spring are secured to said core wire.

16. The guidewire of claim 13 wherein said second helical coil spring is formed from a radiopaque material.

17. The guidewire of claim 13, further comprising:
a rounded tip portion at said distal end of said first helical coil spring and core wire,
wherein said distal end of said second helical coil spring is secured to said tip portion.

* * * * *

UNITED STATES PATENT AND TRADEMARK OFFICE
CERTIFICATE OF CORRECTION

PATENT NO.   : 5,345,945
DATED        : September 13, 1994
INVENTOR(S)  : William S. Hodgson et al.

It is certified that error appears in the above-identified patent and that said Letters Patent is hereby corrected as shown below:

<u>Title page,</u>
Item [22], Filed:, change "Dec. 25, 1993", to read -- Oct. 25, 1993 --.

Signed and Sealed this

Twenty-seventh Day of August, 2002

Attest:

Attesting Officer

JAMES E. ROGAN
Director of the United States Patent and Trademark Office